United States Patent
Kim et al.

(10) Patent No.: US 9,145,586 B2
(45) Date of Patent: Sep. 29, 2015

(54) METHOD OF LABELING A TARGET NUCLEIC ACID

(71) Applicant: Samsung Electronics Co., Ltd., Suwon-si, Gyeonggi-do (KR)

(72) Inventors: Sea-hee Kim, Seoul (KR); Joo-won Rhee, Yongin-si (KR); Ko-bong Choi, Osan-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 119 days.

(21) Appl. No.: 13/904,769

(22) Filed: May 29, 2013

(65) Prior Publication Data

US 2014/0147840 A1 May 29, 2014

(30) Foreign Application Priority Data

Nov. 29, 2012 (KR) .......................... 10-2012-0137335

(51) Int. Cl.
*C12Q 1/68* (2006.01)
*C12P 19/34* (2006.01)

(52) U.S. Cl.
CPC .................................. *C12Q 1/6844* (2013.01)

(58) Field of Classification Search
CPC .......... C12Q 1/25; C12Q 1/48; C12Q 1/6837; C12Q 2521/00; C12Q 2521/50; C12Q 2525/00; C12Q 2533/00; C12Q 2533/101; C12Q 2563/107; G01N 21/01; G01N 21/6486
See application file for complete search history.

(56) References Cited

U.S. PATENT DOCUMENTS

| | | | |
|---|---|---|---|
| 2001/0009762 A1 | 7/2001 | Ach | |
| 2005/0123943 A1 | 6/2005 | Cao et al. | |
| 2008/0300142 A1* | 12/2008 | Getts et al. | 506/9 |
| 2009/0311754 A1 | 12/2009 | Seitz | |
| 2012/0071332 A1 | 3/2012 | Busk | |

FOREIGN PATENT DOCUMENTS

| | | |
|---|---|---|
| JP | 2002-238575 A | 8/2002 |
| JP | 2010-048566 A | 3/2010 |

OTHER PUBLICATIONS

Martin et al., "Tailing and 3'—end Labeling of RNA with Yeast Poly(A) Polymerase and Various Nucleotides," *RNA*, 4: 226-230 (1998).

* cited by examiner

*Primary Examiner* — Young J Kim
(74) *Attorney, Agent, or Firm* — Leydig, Voit & Mayer, Ltd.

(57) ABSTRACT

Methods of labeling and detecting a target nucleic acid by incubating a target nucleic acid with a terminal transferase to extend a terminus of the target nucleic acid and provide an extended region; hybridizing the extended region of the target nucleic acid with a template polynucleotide having a nucleotide sequence complementary to the extended region to obtain a hybridization product; and incubating the hybridization product with a nucleic acid polymerase and either a deoxynucleotide triphosphate (dNTP) having a detectable label or nucleotide triphosphate (NTP) having a detectable label to further extend the extended target nucleic acid.

16 Claims, 5 Drawing Sheets

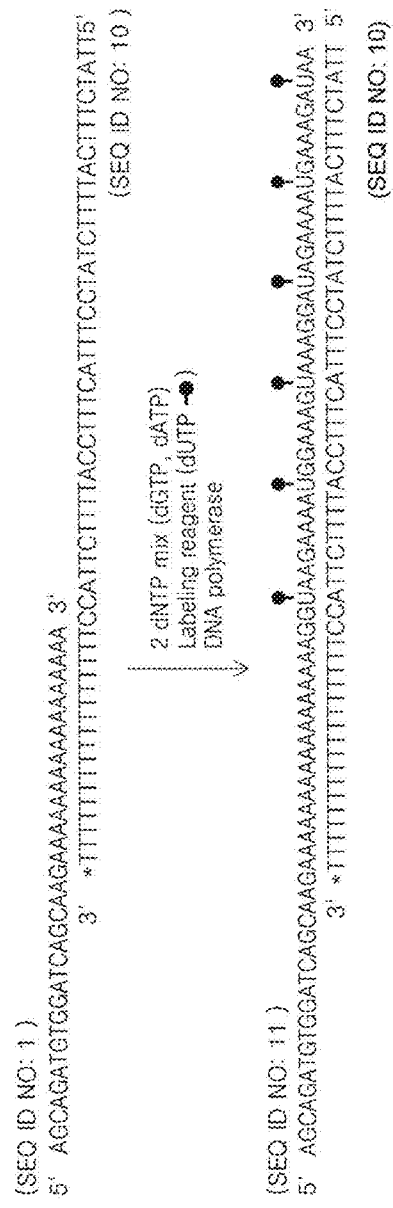

SEQUENCE LISTING

```
<160> NUMBER OF SEQ ID NOS: 11

<210> SEQ ID NO 1
<211> LENGTH: 45
<212> TYPE: DNA
<213> ORGANISM: Artificial Sequence
<220> FEATURE:
<223> OTHER INFORMATION: Synthetic (target nucleic acid)

<400> SEQUENCE: 1
agcagatgtg gatcagcaag aaaaaaaaaa aaaaaaaaaa aaaaa            45
```

<210> SEQ ID NO 2
<211> LENGTH: 120
<212> TYPE: DNA
<213> ORGANISM: Artificial Sequence
<220> FEATURE:
<223> OTHER INFORMATION: Synthetic (template_0)

<400> SEQUENCE: 2
ttttctttcc ttttctttcc ttttctttcc ttttctttcc ttttctttcc ttttctttcc      60
ttttctttcc ttttctttcc ttttctttcc ttttctttcc tttttttttt tttttttttt     120

<210> SEQ ID NO 3
<211> LENGTH: 120
<212> TYPE: DNA
<213> ORGANISM: Artificial Sequence
<220> FEATURE:
<223> OTHER INFORMATION: Synthetic (template_1)

<400> SEQUENCE: 3
ttttctttcc ttttctttcc ttttctttcc ttttctttcc ttttctttcc ttttctttcc      60
ttttctttcc ttttctttcc ttttctttcc ttttctatcc tttttttttt tttttttttt     120

<210> SEQ ID NO 4
<211> LENGTH: 120
<212> TYPE: DNA
<213> ORGANISM: Artificial Sequence
<220> FEATURE:
<223> OTHER INFORMATION: Synthetic (template_4)

<400> SEQUENCE: 4
ttttctttcc ttttctttac ttttctttcc ttttctttcc ttttatttcc ttttctttcc      60
ttttctttcc atttctttcc ttttctttcc ttttctatcc tttttttttt tttttttttt     120

<210> SEQ ID NO 5
<211> LENGTH: 120
<212> TYPE: DNA
<213> ORGANISM: Artificial Sequence
<220> FEATURE:
<223> OTHER INFORMATION: Synthetic (template_6)

<400> SEQUENCE: 5
ttttctttcc tattctttcc ttttctttac ttttctttcc ttttcattcc ttttctttcc      60
ttatctttcc ttttctttca ttttctttcc ttttctatcc tttttttttt tttttttttt     120

<210> SEQ ID NO 6
<211> LENGTH: 120
<212> TYPE: DNA
<213> ORGANISM: Artificial Sequence
<220> FEATURE:
<223> OTHER INFORMATION: Synthetic (template_8)

<400> SEQUENCE: 6
ttttcattcc ttttctttac ttttctttcc tattctttcc ttttatttcc ttttcttacc      60
ttttctttcc atttctttcc tttactttcc ttttctatcc tttttttttt tttttttttt     120

<210> SEQ ID NO 7
<211> LENGTH: 120
<212> TYPE: DNA
<213> ORGANISM: Artificial Sequence
<220> FEATURE:
<223> OTHER INFORMATION: Synthetic (template_10)

<400> SEQUENCE: 7
ttttctatcc ttttctatcc ttttctatcc ttttctatcc ttttctatcc ttttctatcc    60
ttttctatcc ttttctatcc ttttctatcc ttttctatcc tttttttttt tttttttttt   120

<210> SEQ ID NO 8
<211> LENGTH: 120
<212> TYPE: DNA
<213> ORGANISM: Artificial Sequence
<220> FEATURE:
<223> OTHER INFORMATION: Synthetic (template_15)

<400> SEQUENCE: 8
atttcattcc ttatctttca ttttctatcc tttactttcc atttcttacc ttttatttcc    60
tattctttac ttttcattcc ttatctttca ttttctatcc tttttttttt tttttttttt   120

<210> SEQ ID NO 9
<211> LENGTH: 120
<212> TYPE: DNA
<213> ORGANISM: Artificial Sequence
<220> FEATURE:
<223> OTHER INFORMATION: Synthetic (template_20)

<400> SEQUENCE: 9
tattctatcc tattctatcc tattctatcc tattctatcc tattctatcc tattctatcc    60
tattctatcc tattctatcc tattctatcc tattctatcc tttttttttt tttttttttt   120

<210> SEQ ID NO 10
<211> LENGTH: 58
<212> TYPE: DNA
<213> ORGANISM: Artificial Sequence
<220> FEATURE:
<223> OTHER INFORMATION: Synthetic

<400> SEQUENCE: 10
tttttttttt ttttttcca ttcttttacc tttcatttcc tatcttttac tttctatt       58

<210> SEQ ID NO 11
<211> LENGTH: 78
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (40)..(40)
<223> OTHER INFORMATION: Labeling reagent (dUTP)
<220> FEATURE:
<221> NAME/KEY: misc_feature
<222> LOCATION: (48)..(48)
<223> OTHER INFORMATION: Labeling reagent (dUTP)
<220> FEATURE:
<221> NAME/KEY: misc_feature
<222> LOCATION: (55)..(55)
<223> OTHER INFORMATION: Labeling reagent (dUTP)
<220> FEATURE:
<221> NAME/KEY: misc_feature
<222> LOCATION: (62)..(62)
<223> OTHER INFORMATION: Labeling reagent (dUTP)
<220> FEATURE:
<221> NAME/KEY: misc_feature
<222> LOCATION: (69)..(69)
<223> OTHER INFORMATION: Labeling reagent (dUTP)
<220> FEATURE:
<221> NAME/KEY: misc_feature
<222> LOCATION: (76)..(76)
<223> OTHER INFORMATION: Labeling reagent (dUTP)

<400> SEQUENCE: 11

```
agcagatgtg gatcagcaag aaaaaaaaaa aaaaaaaggn aagaaaangg aaagnaaagg    60
anagaaaang aaaganaa                                                  78
```

METHOD OF LABELING A TARGET NUCLEIC ACID

CROSS-REFERENCE TO RELATED APPLICATIONS

This application claims the benefit of Korean Patent Application No. 10-2012-0137335, filed on Nov. 29, 2012, in the Korean Intellectual Property Office, the entire disclosure of which is incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 3,562 Byte ASCII (Text) file named "712610_ST25.txt," created on May 28, 2013.

BACKGROUND

1. Field

The present disclosure relates to methods for labeling target nucleic acids using template polynucleotides, methods of detecting target nucleic acids using the labeled target nucleic acids, and methods of detecting target nucleic acids complementary to probe nucleic acids using the labeled target nucleic acids.

2. Description of the Related Art

The pattern of genes expressed in a cell or tissue is referred to as a gene expression profile. A gene expression profile may differ depending on the type of cell or tissue, and may differ over time. Also, the gene expression profile of a particular cell may be very different from that of a normal cell due to bodily changes such as diseases.

A DNA microarray is a powerful tool for analyzing the gene expression profile. The DNA microarray with probes immobilized on a substrate may detect signals produced due to binding of the probes to target materials. DNA microarrays are used in various fields such as gene function analysis and diagnostic tests for genetic diseases in the medical field, as well as in the environmental field.

For the medical and the research fields, nucleic acids existing in small quantities need to be detected. In end labeling, one label is introduced for one nucleic acid, and accordingly, a nucleic acid existing in small quantity is difficult to detect. If nucleic acids in a sample are amplified for detection, quantification of the nucleic acids may be difficult due to an amplification bias.

Hence, a method of sensitive detection of a nucleic acid present in small quantities in a sample is needed.

SUMMARY

According to an aspect of the present invention, there is provided a method of labeling a target nucleic acid using a template nucleotide.

According to another aspect of the present invention, there is provided a method of detecting a target nucleic acid using the labeled target nucleic acid.

According to another aspect of the present invention, there is provided a method of detecting a target nucleic acid complementary to a probe polynucleotide using the labeled target nucleic acid.

According to an aspect of the present invention, there is provided a method of labeling a target nucleic acid, the method including incubating the target nucleic acid in the presence of a terminal transferase to extend a terminal of the target nucleic acid to have an extended region; hybridizing the extended region of the target nucleic acid with a template polynucleotide having nucleotide sequences complementary to the extended region to obtain a hybridization product; and incubating the hybridization product in the presence of a nucleic acid polymerase and either a deoxynucleotide triphosphate (dNTP) having a detectable label or nucleotide triphosphate (NTP) having a detectable label to further extend the extended target nucleic acid.

The incubating of the target nucleic acid in the presence of the terminal transferase may be performed in the presence of one type of dNTPs or one type of NTPs. The one type of dNTP (or NTP) may be, for example, dATP (or ATP), dGTP (or GTP), dCTP (or CTP), or dTTP (or TTP). The terminal transferase may be an enzyme catalyzing a phosphodiester bond between a 3'-terminal hydroxyl group of the target nucleic acid and a 5'-terminal phosphate group of dNTP or NTP, without a template. The terminal transferase may be, for example, a poly(A) polymerase. The incubating may be performed under conditions in which an extension reaction of the target nucleic acid by the terminal transferase may occur efficiently. The incubating, for example, may be performed with a cofactor such as cobalt.

The target nucleic acid may include DNA, RNA, or a combination thereof.

The target nucleic acid may be, for example, a double stranded nucleic acid. The double stranded nucleic acid may be, for example, a double stranded DNA. If the target nucleic acid is a double stranded DNA, the method may further include denaturing the target nucleic acid to form single stranded nucleic acids. The denaturing may be, for example, processed before hybridizing the target nucleic acid having an extended end region with the template polynucleotide having nucleotide sequences complementary to the extended region. The target nucleic acid may be, for example, a single-stranded nucleic acid. The single-stranded nucleic acid may be, for example, DNA or RNA. The single-stranded DNA may be, for example, obtained by denaturing the double-stranded DNA.

The template polynucleotide may be DNA, RNA, PNA, LNA, or a combination thereof. A 3'-terminal region of the template polynucleotide may include nucleotide sequences complementary to the extended region of the target nucleic acid. For example, if the extended region of the target nucleic acid is composed of polyadenine, a 3'-terminal of the target polynucleotide may be composed of polythimine.

The 3'-terminal of the template polynucleotide may be modified not to be extendable by a nucleic acid polymerase. For example, a 3'-hydroxyl group of a nucleotide located at the 3'-terminal of the template polynucleotide may be modified to a 3'-phosphate group. For example, the 3'-terminal of the target polynucleotide may be modified with C6-amine, C3-spacer, C6-spacer or C12-spacer. The * symbol in FIGS. 1 and 2 represent a DNA polymerase blocker.

The template polynucleotide may include one particular nucleotide (referred to herein as an "identical nucleotide") that repeats at regular intervals in a non-hybridizing region. The template polynucleotide may include different nucleotides between each identical nucleotide. For example, if the identical nucleotide is adenosine monophosphate, the nucleotide included between two adenosine monophosphates may be selected from the group consisting of guanosine monophosphate, thymidine monophosphate, cytidine monophosphate, or a combination thereof. The template polynucleotide may include the identical nucleotide at every 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In the step of further extending the extended target nucleic acid by incubating the hybridization product with a dNTP having a detectable label or an NTP having a detectable label and a nucleic acid polymerase, one type of dNTP or one type of NTP may have a detectable label. The dNTP having the detectable label or the NTP having the detectable label may be complementary to the identical nucleotide of the template polynucleotide. For example, if the identical nucleotide of the template polynucleotide is adenosine monophosphate, the dNTP having the detectable label or the NTP having the detectable label may be deoxythymidine triphosphate (dTTP) or uridine triphosphate (UTP). The identical nucleotides that repeat in the template polynucleotide may allow the dNTPs or NTPs having the detectable label to be located in the counterpart of the repeated position. Using the template polynucleotide where the identical nucleotides repeat enables the target nucleic acid to be multi-labeled with an intended number of detectable labels incorporated. The detectable label may be a biotin or a fluorescent dye. The biotin, for example, may release a signal by binding to streptavidin PE (phycoerythrin-conjugated streptavidin). The fluorescent dye, for example, may be selected from the group consisting of fluorescein, FITC, Alexa Fluor 488, GFP, CFSE, CFDA-SE, DyLight 488, PE, PI, PerCP, PerCP-Cy5.5, PE-Alexa Fluor 700, PE-Cy5 (TRI-COLOR), PE-Cy5.5, PE-Alexa Fluor 750, PE-Cy7, APC, APC-Cy7, APC-eFluor 780, Alexa Fluor 700, Cy5, Draq-5, Pacific Orange, Amine Aqua, Pacific Blue, DAPI, Alexa Fluor 405, eFluor 450, eFluor 605 Nanocrystals, eFluor 625 Nanocrystals, and eFluor 650 Nanocrystals.

According to another aspect of the present invention, there is provided a method of detecting the target nucleic acid, the method including incubating the target nucleic acid in the presence of a terminal transferase to extend a terminal of the target nucleic acid to have an extended region; hybridizing the extended region of the target nucleic acid with a template polynucleotide having nucleotide sequences complementary to the extended region to obtain a hybridization product; incubating the hybridization product in the presence of a nucleic acid polymerase and either a dNTP having a detectable label or an NTP having a detectable label to further extend the extended target nucleic acid; and measuring a signal from the detectable label of the further extended target nucleic acid.

Incubating the target nucleic acid in the presence of a terminal transferase to extend a terminal of the target nucleic acid to have an extended region; hybridizing the extended region of the target nucleic acid with a template polynucleotide having a nucleotide sequence complementary to the extended region to obtain a hybridization product; and incubating the hybridization product in the presence of a nucleic acid polymerase and either a dNTP having a detectable label or an NTP having a detectable label to further extend the extended target nucleic acid are the same as the above.

The target nucleic acid may, for example, include a polymerase chain reaction (PCR) product obtained by using a primer that may amplify a specific gene. The target nucleic acid may, for example, include a single-stranded nucleic acid obtained by denaturing the PCR product.

The detectable label may be, for example, a biotin or a fluorescein. If the detectable label is biotin, measuring the signal may involve, for example, confirming color formation and an amount of the color formation corresponding to degradation of substrate by an enzyme bound to biotin or confirming a presence and an amount of light released from streptavidin PE by binding the streptavidin PE to biotin. If the detectable label is fluorescein, measuring the signal may involve, for example, confirming a presence and an amount of fluorescent signal through a fluorescent microscope. From the measured signal, a presence and an amount of the target nucleic acid may be confirmed.

According to another aspect of the present invention, there is provided a method of detecting a target nucleic acid complementary to a probe polynucleotide, the method including incubating the target nucleic acid in the presence of a terminal transferase to extend a terminal of the target nucleic acid to have an extended region; hybridizing the extended region of the target nucleic acid with a template polynucleotide having a nucleotide sequence complementary to the extended region to obtain a hybridization product; incubating the hybridization product in the presence of a nucleic acid polymerase and either a dNTP having a detectable label or an NTP having a detectable label to further extend the extended target nucleic acid; hybridizing the further extended target nucleic acid with a probe polynucleotide having nucleotide sequences complementary to a non-extended region of the further extended target nucleic acid to obtain a further extended target nucleic acid hybridized with the probe; and measuring a signal from the detectable label of the further extended target nucleic acid hybridized with the probe.

Incubating the target nucleic acid in the presence of a terminal transferase to extend a terminal of the target nucleic acid to have an extended region; hybridizing the extended region of the target nucleic acid with a template polynucleotide having nucleotide sequences complementary to the extended region to obtain a hybridization product; incubating the hybridization product in the presence of a nucleic acid polymerase and either a dNTP having a detectable label or an NTP having a detectable label to further extend the extended target nucleic acid are the same as the above.

The target nucleic acid may be, for example, a cDNA obtained by a reverse transcription of RNA extracted from a specific tissue. The probe polynucleotide may be, for example, an oligonucleotide including a part of gene expressed in a specific tissue, an oligonucleotide complementary to the same, single-stranded cDNA fragment obtained from mRNA of the gene, or complementary cDNA thereof.

The method may further include denaturing the hybridization product including the further extended target nucleic acid to form single-stranded nucleic acids.

The probe polynucleotides may be, for example, immobilized on a substrate. The substrate may have an array form where at least two probe polynucleotides are immobilized on immobilization regions. The probe polynucleotides may be covalently bonded to each immobilization regions. If the probe polynucleotides are immobilized on the substrate, the method may further include washing the substrate after hybridizing the further extended target nucleic acids with the probe polynucleotides.

The detectable label is the same as the above. From the measured signal, the presence and the amount of the target nucleic acid complementary to the probe polynucleotide may be confirmed.

According to an aspect of the present invention, labeling a target nucleic acid may efficiently label the target nucleic acid.

According to another aspect of the present invention, detecting the target nucleic acid may efficiently detect the target nucleic acid.

According to another aspect of the present invention, detecting a target nucleic acid complementary to a probe nucleotide may efficiently detect the target nucleic acid complementary to the probe nucleotide.

BRIEF DESCRIPTION OF THE DRAWINGS

These and/or other aspects will become apparent and more readily appreciated from the following description of the embodiments, taken in conjunction with the accompanying drawings in which:

FIG. 2 is a mimetic diagram showing an action of a template polynucleotide to label a nucleic acid.

DETAILED DESCRIPTION

Figure 1:
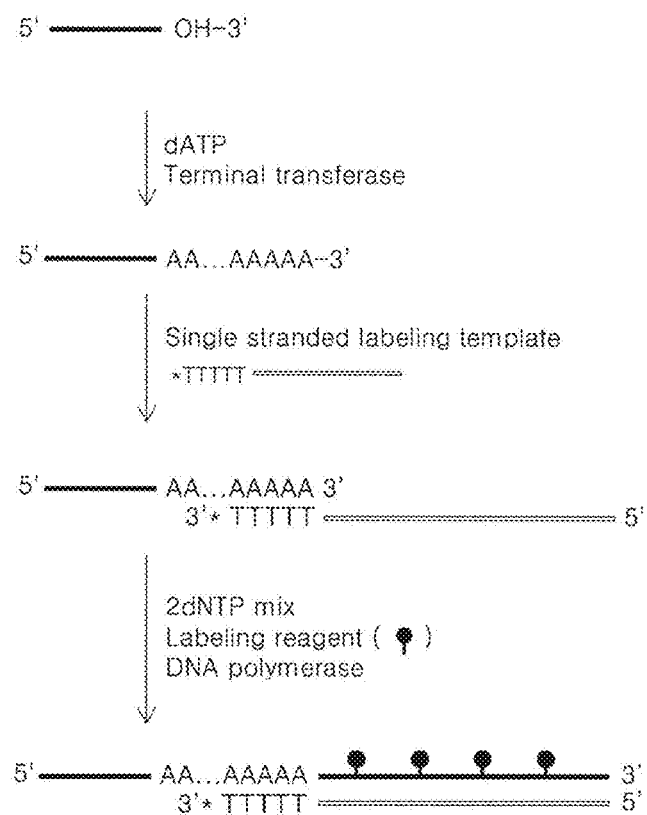
FIG. 1 is a mimetic diagram showing the labeling of a nucleic acid by using a template polynucleotide.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

EXAMPLE 1

Preparing a Target Nucleic Acid and Template Polynucleotides

A 45 nucleotide (nt) polynucleotide having a nucleotide sequence of SEQ ID NO: 1 including a 25 nt polyadenine sequence at the 3-terminal was prepared as a target nucleic acid. 8 types of template polynucleotides were prepared, having nucleotide sequences of SEQ ID NO: 2 to 9 and including 20 nt polythymine sequences at their 3'-terminals. Each template polynucleotide was composed of adenosine at every 5, 7, 10, 13, 17, or 26 nucleotides, and the rest of each template polynucleotide was composed of cytosine and thymine.

Each of the target polynucleotides having SEQ ID NO: 2 to 9 included 0, 1, 4, 6, 8, 10, 15, or 20 adenosine nucleotides (hereinafter, also referred to as "template polynucleotide_0, 1, 4, 6, 8, 10, 15, or 20).

EXAMPLE 2

3'-Terminal Labeling of Target Nucleic Acids 10 ng of 45 nt target nucleic acids and 100 ng of a template polynucleotide were incubated for 10 minutes at a temperature of 80° C. with a buffer including 50 mM of NaCl, 10 mM of Tris-HCl, 10 mM of $MgCl_2$, and 1 mM of dithiothreitol to prepare a reaction mixture. Thereafter, the reaction mixture was cooled on ice for about 1 minute to about 2 minutes and incubated for 10 minutes at a temperature of 37° C. Thereafter, 2dNTP mixture including dATP and dGTP having a final concentration of 0.25 mM, cyanine 3-dUTP having a final concentration of 0.2 mM, and 1 unit of Klenow fragment were added to the mixture and incubated for 30 minutes at a temperature of 37° C. The reaction product was electrophoresed in a 10% denaturing gel.

Figure 3A:
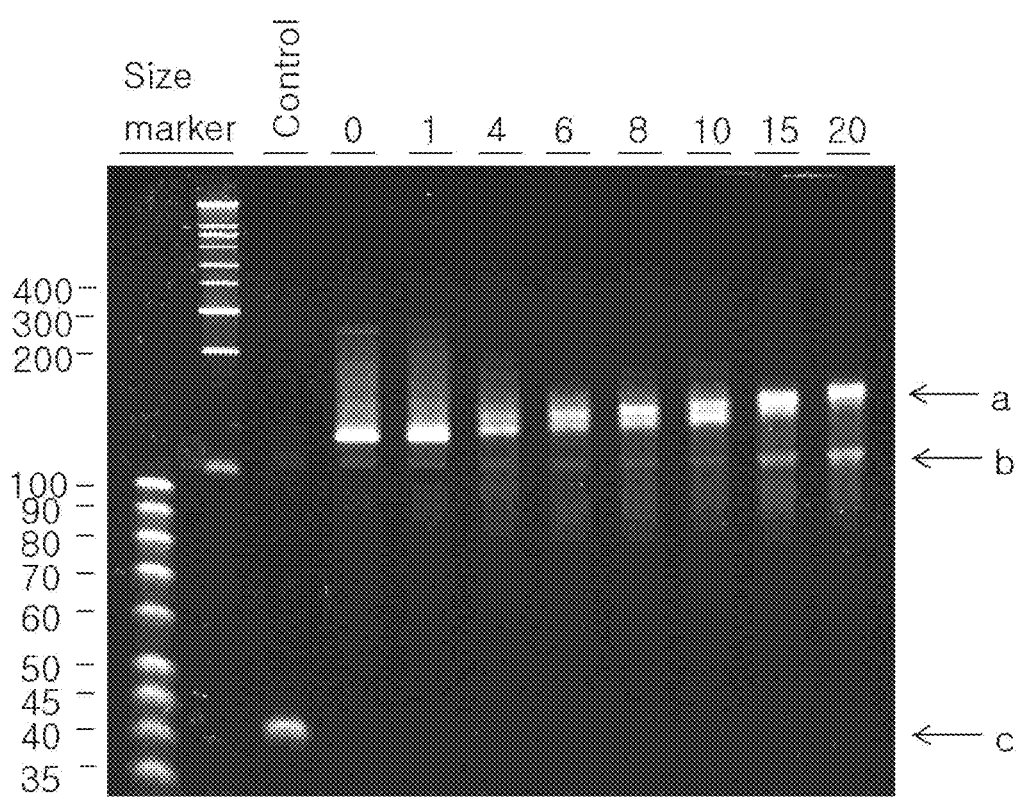
FIG. 3A is a gel image that shows a result of electrophoresis after labeling a target nucleic acid using 8 types of template polynucleotides.

FIG. 3A shows a result of electrophoresis after labeling a target nucleic acid using 8 types of template polynucleotides. The electrophoresed gel was stained for 10 minutes using 1×SYBR® Gold Nucleic Acid Gel Stain (Invitrogen) and confirmed that the nucleic acid was extended. In FIG. 3A, (a) shows 145 nt target nucleic acid labeled with 0, 1, 4, 6, 8, 10, 15, or 20 of Cy3 in each lane 0, 1, 4, 6, 8, 10, 15, or 20. As the number of label increases, movement of the target nucleic acid slows, showing an efficient labeling of the target nucleic acid. In FIG. 3A, (b) 120 nt template polynucleotide_0, 1, 4, 6, 8, 10, 15, or 20, and (c) shows non-labeled 45 nt target nucleic acid.

Figure 3B:
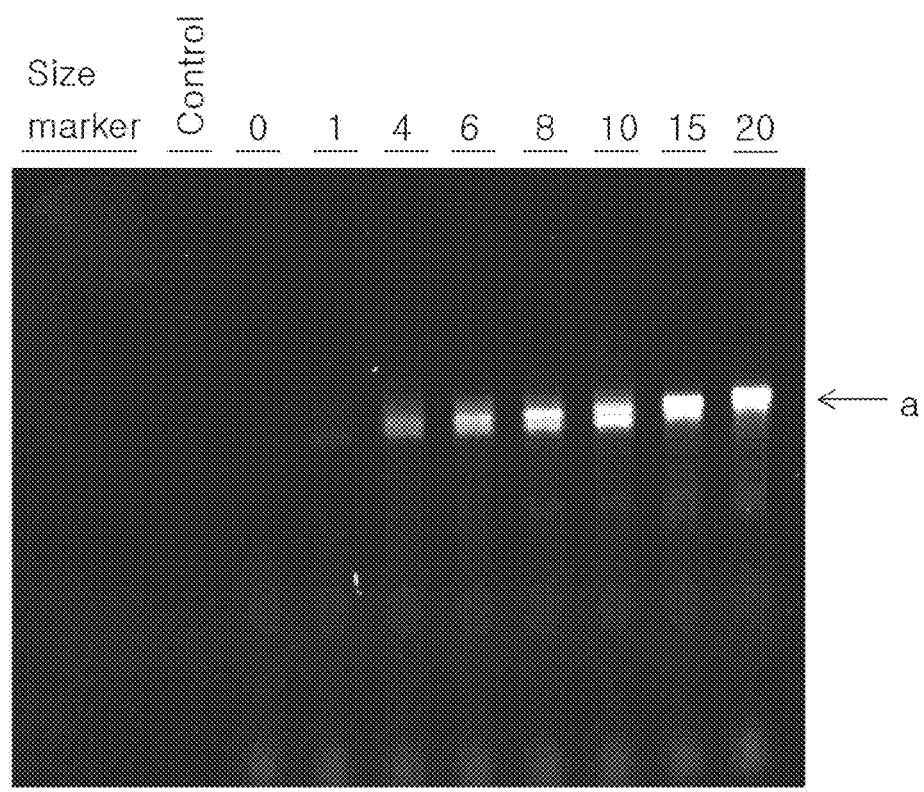
FIG. 3B is a gel image shows a result of measuring fluorescent signals after labeling a target nucleic acid using 8 types of target polynucleotides and electrophoresing.

FIG. 3B shows the result of measuring fluorescent signals after labeling a target nucleic acid by using 8 types of target polynucleotides and electrophoresis. In FIG. 3B, (a) shows 145 nt target nucleic acid labeled with 0, 1, 4, 6, 8, 10, 15, or 20 of Cy3 in each lane 0, 1, 4, 6, 8, 10, or 15. As the number of label increases, a magnitude of the fluorescent signal increased, showing an efficient labeling of the target nucleic acid.

Figure 3C:
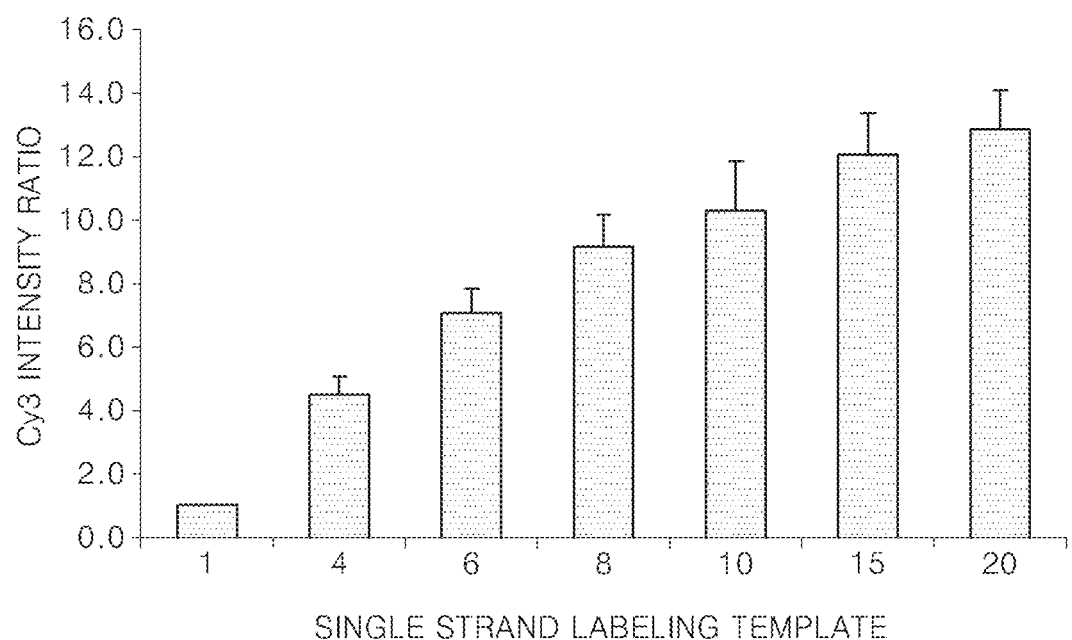
FIG. 3C is a graph that shows a result of comparing sizes of fluorescent signals measured in FIG. 3B.

FIG. 3C shows the result of comparing the magnitude of fluorescent signals measured in FIG. 3B. With the assumption that a magnitude of a fluorescent signal from one labeled nucleotide in the extended region of the target nucleic acid is equal to 1, a magnitude of a fluorescent signal from the 20 labeled nucleotides increased by 13 times. Until one nucleotide is labeled per 10 nucleotides, magnitudes of fluorescent signals were higher in proportion to the number of the labeled nucleotides.

It should be understood that the exemplary embodiments described herein should be considered in a descriptive sense only and not for purposes of limitation. Descriptions of features or aspects within each embodiment should typically be considered as available for other similar features or aspects in other embodiments.

---

What is claimed is:

1. A method of labeling a target nucleic acid, the method comprising:
incubating a target nucleic acid with a terminal transferase to extend a terminus of the target nucleic acid and provide an extended region;
hybridizing the extended region of the target nucleic acid with a template polynucleotide having a nucleotide sequence complementary to the extended region to obtain a hybridization product; and
incubating the hybridization product with a nucleic acid polymerase and either a deoxynucleotide triphosphate (dNTP) having a detectable label or nucleotide triphosphate (NTP) having a detectable label to further extend the extended target nucleic acid.

2. The method of claim 1, wherein the incubating of the target nucleic acid with the terminal transferase is performed in the presence of one type of dNTPs or one type of NTPs.

3. The method of claim 1, wherein the incubating of the target nucleic acid with the terminal transferase comprises extending the 3'-terminal of the target nucleic acid.

4. The method of claim 1, wherein the target nucleic acid is DNA, RNA, or a combination thereof.

5. The method of claim 1, wherein the method further comprises denaturing the target nucleic acid to form single stranded nucleic acids.

6. The method of claim 1, wherein the template polynucleotide is DNA, RNA, PNA, LNA, or a combination thereof.

7. The method of claim 6, wherein the 3'-terminal of the template polynucleotide is modified and not extendable by the nucleic acid polymerase.

8. The method of claim 6, wherein the template polynucleotide includes a nucleotide that repeats at a regular interval, wherein the interval is every 4, 5, 6, 7, 8, 9, 10, 11, 12, 13, 14, 15, 16, 17, 18, 19, 20, 21, 22, 23, 24, 25, 26, 27, 28, 29, or 30 nucleotides.

9. The method of claim 8, wherein the dNTP having the detectable label or the NTP having the detectable label is complementary to the nucleotide that repeats at a regular interval in the template polynucleotide.

10. The method of claim 1, wherein incubating the hybridization product to further extend the extended target nucleic acid is performed in the presence of one type of dNTP having a detectable label or one type of NTP having a detectable label.

11. The method of claim 1, wherein the detectable label is biotin or a fluorescent dye.

12. A method of detecting a target nucleic acid, the method comprising:
incubating the target nucleic acid with a terminal transferase to extend a terminus of the target nucleic acid and provide an extended region;
hybridizing the extended region of the target nucleic acid with a template polynucleotide having a nucleotide sequence complementary to the extended region to obtain a hybridization product;
incubating the hybridization product with a nucleic acid polymerase and either a dNTP having a detectable label or an NTP having a detectable label to further extend the extended target nucleic acid; and
measuring a signal from the detectable label of the further extended target nucleic acid.

13. The method of claim 12, wherein the target nucleic acid comprises a polymerase chain reaction (PCR) product.

14. A method of detecting a target nucleic acid, the method comprising:
incubating the target nucleic acid with a terminal transferase to extend a terminus of the target nucleic acid and provide an extended region;
hybridizing the extended region of the target nucleic acid with a template polynucleotide having a nucleotide sequence complementary to the extended region to obtain a hybridization product, wherein the 3'-terminal of the template polynucleotide is modified and not extendable by a nucleic acid polymerase;
incubating the hybridization product with a nucleic acid polymerase and either a dNTP having a detectable label or an NTP having a detectable label to further extend the extended target nucleic acid;
hybridizing the further extended target nucleic acid with a probe polynucleotide having a nucleotide sequence complementary to a non-extended region of the further extended target nucleic acid to obtain a further extended target nucleic acid hybridized with the probe; and
measuring a signal from a detectable label of the further extended target nucleic acid hybridized with the probe.

15. The method of claim 14, wherein the method further comprises denaturing the hybridization product including the further extended target nucleic acid to form single-stranded nucleic acids.

16. The method of claim 15, wherein the probe polynucleotide is immobilized on a substrate.

* * * * *